(12) United States Patent
Crawford et al.

(10) Patent No.: US 9,364,359 B2
(45) Date of Patent: Jun. 14, 2016

(54) SYSTEMS AND METHODS FOR DELIVERY OF A MEDICAL DEVICE

(71) Applicant: W. L. Gore & Associates, Inc., Newark, DE (US)

(72) Inventors: Daniel A. Crawford, Flagstaff, AZ (US); Logan R. Hagaman, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 247 days.

(21) Appl. No.: 13/692,755

(22) Filed: Dec. 3, 2012

(65) Prior Publication Data

US 2013/0150945 A1 Jun. 13, 2013

Related U.S. Application Data

(60) Provisional application No. 61/568,412, filed on Dec. 8, 2011.

(51) Int. Cl.
*A61F 2/95* (2013.01)
*A61F 2/966* (2013.01)
*A61F 2/97* (2013.01)

(52) U.S. Cl.
CPC . *A61F 2/966* (2013.01); *A61F 2/95* (2013.01); *A61F 2/97* (2013.01); *A61F 2002/9511* (2013.01)

(58) Field of Classification Search
CPC ..... A61F 2/95; A61F 2/97; A61F 2002/9511; A61F 2/06; A61F 2/07; A61F 2/92; A61F 2/962; A61F 2/966; A61F 2002/9665
See application file for complete search history.

(56) References Cited

U.S. PATENT DOCUMENTS

| | | | | |
|---|---|---|---|---|
| 4,913,141 A * | 4/1990 | Hillstead | ...................... | 623/1.11 |
| 5,290,305 A * | 3/1994 | Inoue | .............................. | 623/1.2 |
| 5,387,235 A * | 2/1995 | Chuter | ......................... | 623/1.11 |
| 5,405,378 A * | 4/1995 | Strecker | ...................... | 623/1.12 |
| 5,873,906 A * | 2/1999 | Lau et al. | ...................... | 128/898 |
| 5,948,017 A * | 9/1999 | Taheri | ......................... | 623/1.14 |
| 6,302,891 B1 * | 10/2001 | Nadal | ..................... | A61F 2/962 |
| | | | | 606/108 |
| 6,352,553 B1 * | 3/2002 | van der Burg et al. | ....... | 623/1.23 |
| 6,352,561 B1 * | 3/2002 | Leopold et al. | .............. | 623/1.23 |
| 7,837,729 B2 | 11/2010 | Gordon et al. | | |

(Continued)

FOREIGN PATENT DOCUMENTS

| WO | 01/74270 | 10/2001 |
|---|---|---|
| WO | 2009/148594 | 12/2009 |

(Continued)

OTHER PUBLICATIONS

Annex to Form PCT/ISA/206 Communication Relating to the Results of the Partial International Search for PCT/US2012/067758 mailed Mar. 18, 2013, corresponding to U.S. Appl. No. 13/692,755.

*Primary Examiner* — Ryan J Severson
*Assistant Examiner* — Christian Knass (57) ABSTRACT

In various embodiments, the medical device delivery system described herein can be configured to position and deliver a medical device in a body lumen. The medical device delivery system can comprise an elongate member, a medical device and a leash. During deployment, the medical device can be tethered to the catheter by the leash, to stabilize and prevent unwanted shifting of the medical device as it deploys at the treatment site.

22 Claims, 5 Drawing Sheets

(56) References Cited

U.S. PATENT DOCUMENTS

| | | | |
|---|---|---|---|
| 2002/0099436 A1* | 7/2002 | Thornton | A61F 2/06 623/1.12 |
| 2003/0088305 A1* | 5/2003 | Van Schie et al. | 623/1.12 |
| 2004/0015224 A1* | 1/2004 | Armstrong et al. | 623/1.12 |
| 2004/0122503 A1* | 6/2004 | Campbell et al. | 623/1.12 |
| 2007/0100427 A1* | 5/2007 | Perouse | 623/1.11 |
| 2007/0293929 A1* | 12/2007 | Aoba et al. | 623/1.11 |
| 2009/0048656 A1 | 2/2009 | Wen | |
| 2009/0189377 A1 | 7/2009 | Vigeant et al. | |
| 2009/0312829 A1* | 12/2009 | Aoba et al. | 623/1.11 |
| 2010/0125322 A1 | 5/2010 | Fitzgerald et al. | |
| 2010/0171295 A1 | 7/2010 | Koh | |
| 2010/0211052 A1 | 8/2010 | Brown et al. | |
| 2010/0280316 A1 | 11/2010 | Dietz et al. | |
| 2010/0331956 A1* | 12/2010 | Armstrong et al. | 623/1.12 |
| 2011/0049852 A1 | 3/2011 | Kibat et al. | |
| 2011/0288624 A1* | 11/2011 | Roeder et al. | 623/1.11 |
| 2012/0022630 A1* | 1/2012 | Wubbeling | A61F 2/95 623/1.11 |
| 2013/0123900 A1* | 5/2013 | Eblacas et al. | 623/1.13 |
| 2014/0046430 A1* | 2/2014 | Shaw | 623/1.12 |

FOREIGN PATENT DOCUMENTS

| | | |
|---|---|---|
| WO | 2010/011698 | 1/2010 |
| WO | 2010/042210 | 4/2010 |
| WO | 2010/090699 | 8/2010 |
| WO | 2010/121049 | 10/2010 |

* cited by examiner

SYSTEMS AND METHODS FOR DELIVERY OF A MEDICAL DEVICE

CROSS-REFERENCE TO RELATED APPLICATIONS

This application claims priority to U.S. Provisional Application Ser. No. 61/568,412, entitled "SYSTEMS AND METHODS FOR DELIVERY OF A MEDICAL DEVICE" and filed Dec. 8, 2011, which is hereby incorporated by reference in its entirety.

BACKGROUND

1. Field

The invention relates to improved medical device delivery systems and methods for positioning a medical device at a desired location in a body lumen. More specifically, the invention relates to improved medical device delivery systems and methods for maintaining the longitudinal position of a medical device during deployment at a desired location in a body lumen.

2. Discussion of the Related Art

Medical procedures that treat conditions endovascularly often require that a medical device be delivered to a treatment region in a compressed configuration. The device must then be expanded to a treatment configuration to contact the vasculature. Often, these devices are compressed by a sheath during delivery. When the sheath is retracted from the device, the device begins to expand. This expansion can occur prior to completely removing the sheath, such that, a distal portion of the medical device expands while the proximal portion of the medical device is still compressed by the sheath.

As a result of the expansion, the medical device may move or shift at the treatment region. Fluids and other conditions at the treatment region may also cause the medical device to move or shift. This shifting and/or moving can make it difficult to effectively position the medical device at the treatment site.

As such, there is a need for a medical device system that minimizes movement and stabilizes a medical device during deployment at a treatment site.

BRIEF DESCRIPTION OF THE DRAWINGS

The subject matter of the present disclosure is particularly pointed out and distinctly claimed in the concluding portion of the specification. A more complete understanding of the present disclosure, however, can best be obtained by referring to the detailed description and claims when considered in connection with the drawing figures, wherein like numerals denote like elements and wherein:

DETAILED DESCRIPTION

A detailed description of various embodiments herein makes reference to the accompanying drawing figures, which show various embodiments and implementations thereof by way of illustration and best mode, and not of limitation. While these embodiments are described in sufficient detail to enable those skilled in the art to practice the embodiments, it should be understood that other embodiments can be realized and that mechanical and other changes can be made without departing from the spirit and scope of the present disclosure. Furthermore, any reference to singular includes plural embodiments, and any reference to more than one component can include a singular embodiment. Moreover, recitation of multiple embodiments having stated features is not intended to exclude other embodiments having additional features or other embodiments incorporating different combinations of the stated features. In describing various embodiments, the term distal is used to denote the end of a device nearest to the treatment region within a patient's body. The term proximal is used to denote the end of a device nearest to the user or operator of the device.

Disclosed is a system for securing a sheath and/or securing a medical device during deployment. In general, the system comprises a delivery catheter, a medical device, a sheath surrounding the medical device, and a leash line connected to the delivery catheter (directly or indirectly, e.g., via an olive).

In various embodiments, the delivery catheter is any device suitable for passage through the vasculature to a treatment region. The delivery catheter provides access and/or passage to a treatment region. In these embodiments, the delivery catheter transports various devices to the treatment region, including, for example, medical devices, tools, lights, and/or any other suitable therapeutic devices.

In various embodiments, the delivery catheter is a flexible, elongated element having proximal and distal ends and is capable of passing through a vessel. The delivery catheter comprises at least one lumen over at least of portion of its length. This lumen provides a user with access to the treatment region. In these embodiments, the delivery catheter can further comprise or be configured to transport elongate members or tools including, for example, guidewires, catheters, optical fibers, or the like. A suitable delivery catheter can comprise a blunt, rounded, or tapered distal tip, to name a few, and can be characterized by varying degrees of rigidity or softness, which can further vary along the length of the delivery catheter. The delivery catheter can have any cross-sectional shape including, for example, a circular shape, an oval shape, a triangular shape, a square shape, a polygon shape, a uniform shape, or a random shape.

A delivery catheter, or any portion thereof, can be comprised of any number of materials including silicone, latex, polyurethanes, polyvinyl chlorides, polyethylenes, polysiloxanes, polycarbonates, nylons, PTFEs, stainless steel, nitinol, or any other biocompatible material, including combinations of the foregoing. Additionally, a delivery catheter, or any portion thereof, can be hydrophilic or hydrophobic.

In various embodiments, the delivery catheter comprises an olive. The olive attaches to the distal end of the delivery catheter. The olive is located near the distal end of the delivery catheter and retains a leash line. In these embodiments, the olive comprises an attachment point, such as, for example, a hole, a knob, an eyelet, or any other mechanism suitably configured to attach and retain a leash line. The olive also defines a channel. The channel can at least partially align with a lumen defined by the delivery catheter. In an embodiment, the channel of the olive facilitates passage of one or more articles, including for example, the medical device, release lines, medical instruments, tools, lights, and/or the like, between the catheter and the treatment site. Moreover, in these embodiments, the olive can be of any suitable size and can have any suitable shape, such as, a rounded or blunt shape.

In various embodiments, the medical device is any suitable structure configured to provide treatment to the vasculature. In operation, the medical device deploys from the delivery catheter at a treatment region in vasculature. During delivery through the delivery catheter, the medical device is in a delivery configuration. Upon deploying from the delivery catheter, the medical device actuates to a treatment configuration. For example, in one embodiment, the medical device expands upon deployment form the delivery catheter and provides support to the vasculature. In other embodiments, the medical device provides other treatment in the vasculature including, for example, monitoring, drug delivery, sample collection, and/or any other suitable treatment.

In various embodiments, the medical device can be any suitable medical device including, for example, a stent, a stent graft, a filter, a valve, a bifurcated stent, an occluder, a drug-delivering device, such as a drug-eluting balloon and/or stent, an oncology therapy, a pressure flow monitor, an energy transmission device, a spacer, an optical device, a marker and/or any other similar endoluminally deliverable device. The medical device comprises one or more attachment mechanisms at its proximal and/or distal end. For example, the medical device can comprise apices, a knob, an eyelet, a hole, or any other suitable attachment mechanism at its proximal and/or distal end. The medical device can also comprise or be covered with any suitable graft material or therapeutic agent. Moreover, in various embodiments, the medical device receives or otherwise couples to the leash line in any suitable fashion to minimize longitudinal movement and facilitate deployment at a treatment region.

In various embodiments, the medical device is comprised of a shape-memory material, such as nitinol. In other embodiments, the medical device is comprised of other materials, self-expandable or otherwise expandable (e.g., with a conventional balloon catheter or spring mechanism), such as various metals (e.g., stainless steel), alloys and polymers.

In various embodiments, the deployment sheath covers the medical device and restrains the medical device toward an outer peripheral dimension or delivery configuration suitable for endoluminal delivery. For example, a stent or stent graft, when implanted in the vasculature, is constrained to a low delivery profile in order to gain access to the treatment site. The deployment sheath can also protect at least a portion of the medical device as the medical device travels with the delivery catheter through the vasculature to the treatment site. As such, the deployment sheath can cover, protect and/or restrain any medical device as it travels with the delivery catheter through the vasculature. In the case of devices that deliver a drug or other therapeutic agent, the delivery sheath can also ensure minimal drug release into the bloodstream during delivery.

In various embodiments, the deployment sheath is any suitable sheath or sleeve that wraps around and constrains the medical device toward a delivery configuration for endoluminal delivery. The deployment sheath is flexible so that it generally conforms to the shape of the medical device and is sufficiently strong to restrain the medical device toward a delivery configuration during deployment to the treatment site.

In various embodiments, a deployment sheath can be axially displaced or removed to reveal the medical device and allow expansion of the medical device at the treatment site.

In various embodiments, the deployment sheath can be made from a flexible film and comprise a series of holes, openings, passages, or eyelets defined along generally opposite sides of the sheath. The sheath can be wrapped around and cover the medical device, and a release line can be threaded through the holes to compress and/or restrain the medical device toward a delivery configuration. During deployment, the release line un-threads from the holes to release the deployment sheath and allow the medical device to expand.

In a number of embodiments, the deployment sheath can be made of any suitable material, including for example, a fluoropolymer such as ePTFE. Alternatively, or in combination with a fluoropolymer, the deployment sheath can be formed of biocompatible materials, such as polymers, which can include fillers such as metals, carbon fibers, Dacron, glass fibers or ceramics. Such polymers can include olefin polymers, polyethylene, polypropylene, polyvinyl chloride, polytetrafluoroethylene which is not expanded, fluorinated ethylene propylene copolymer, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, such as fully or partially halogenated polyethers, copolymers, and combinations thereof. Also, polyesters, including polyethylene terephthalate (PET) polyesters, polypropylenes, polyethylenes, polyurethanes, polyolefins, polyvinyls, polymethylacetates, polyamides, naphthalane dicarboxylene derivatives, and natural silk can be included in the deployment sheath. Further detailed description of suitable deployment sheaths and release lines can be found in U.S. Pat. No. 5,972,441 to Campbell et al., and U.S. Pat. No. 6,352,561 to Leopold et al., the contents of which are incorporated herein by reference.

In general, the leash line secures a sheath and/or secures a medical device during deployment. In one embodiment, the leash line secures the sheath. The leash line can permanently secure the sheath, or only temporarily secure the sheath during deployment of the medical device. For example, in various embodiments, the deployment sheath will remain in vivo post deployment. The leash line secures the sheath in any number of ways, including, but not limited to a knot, loop, clip, adhesive, etc.

In various embodiments, deployment of the medical device releases the leash line from the sheath. In yet other various embodiments, the leash line is released from the sheath remotely by a user. In still other various embodiments, the leash line is bio-resorbable and/or is connected to the medical device with a bio-resorbable filament or adhesive, thereby releasable from the sheath after a specified period of time. In still other various embodiments, the leash line is released by incorporating a shape changing material into the leash line or the sheath (e.g., one that changes shape in response to an external stimuli or condition).

In various embodiments, opening the sheath releases the leash line from the sheath. For example, the sheath can be sewn closed by a removable release line known in the art and the leash line can secure one or more stitches of the release line (e.g., one or more stitches located at or near the proximal/trailing end of the sheath) such that when the secured stitch or stitches are removed, the leash line securing the sheath is released. The leash line can secure one or more stitches of the release line with a knot, loop, clip, etc. In accordance with an aspect of this embodiment, the length of the release line tail determines how long the leash line is attached to the sheath.

In another embodiment, the leash line temporarily secures the medical device during its deployment. The leash line secures the sheath in any number of ways, including, but not limited to a knot, loop, clip, adhesive, etc.

In various embodiments, deployment of the medical device releases the leash line from the medical device. In yet other various embodiments, the leash line is released from the medical device remotely by a user. In still other various embodiments, the leash line is bio-resorbable and/or is connected to the medical device with a bio-resorbable filament or adhesive, thereby releasable from the medical device after a specified period of time. In still other various embodiments, the leash line is released by incorporating a shape changing material into the leash line or the medical device (e.g., one that changes shape in response to an external stimuli or condition).

In various embodiments, opening the deployment sheath releases the leash line from the medical device. For example, the sheath can comprise a removable release line that is connected to the leash line (e.g., threaded through a knot, loop, clip, etc. in the leash line) through an opening of the medical device (e.g., an opening located at or near the proximal/trailing end of the medical device). In this manner, when the release line is removed, the leash line securing the medical device is released. In accordance with an aspect of this embodiment, the length of the release line tail determines how long the leash line is attached to the medical device.

In various embodiments, the leash line is generally configured as a string or tether. In some embodiments, the leash line comprises segments. The segments can be indicated by any suitable mechanism, including, for example, by knots, clips, adhered points, or any other suitable mechanism. For example, the leash line comprises one or more knots that define one or more segments in the leash line. In various embodiments, one or more of these knots are configured with slack. This slack can be used to define one or more loops that attached to the deployment sheath, medical device, or both, to facilitate deployment of the medical device at the treatment site. The leash line can also be of any suitable length to prevent or minimize longitudinal movement between the medical device and the delivery catheter.

In various embodiments, the leash line can be any suitable material having desirable qualities including, for example, materials that are biocompatible, have relatively high tensile strength, and/or do not particulate. For example, the leash line can be made of a fluoropolymer such as ePTFE, Kevlar, which can be wrapped, covered, or otherwise encapsulated with a fluoropolymer, liquid crystal polymers, metals, Dacron, glass fibers, ceramics or the like. In these embodiments, the material is sufficiently flexible and has sufficient tensile strength to facilitate positioning, deployment, and retaining of the medical device. In some embodiments, the leash line can be formed by braiding or knitting the biocompatible material into a sting and/or tether. In other embodiments, the leash line can be extruded or otherwise formed as a single strand of material.

Figure 1:
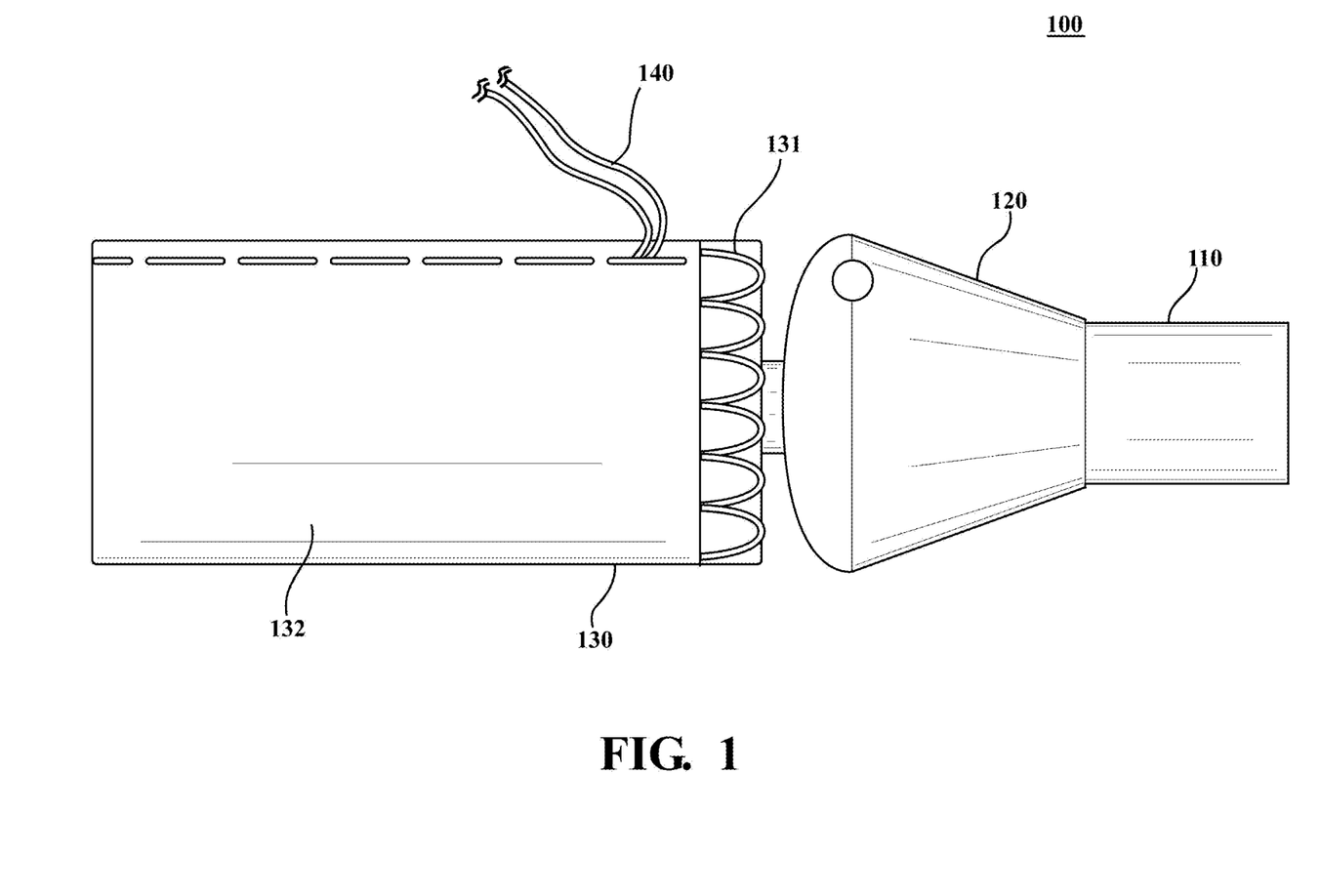
FIGS. 1-5 illustrate a medical device delivery system in accordance with the present disclosure.
Figure 2:
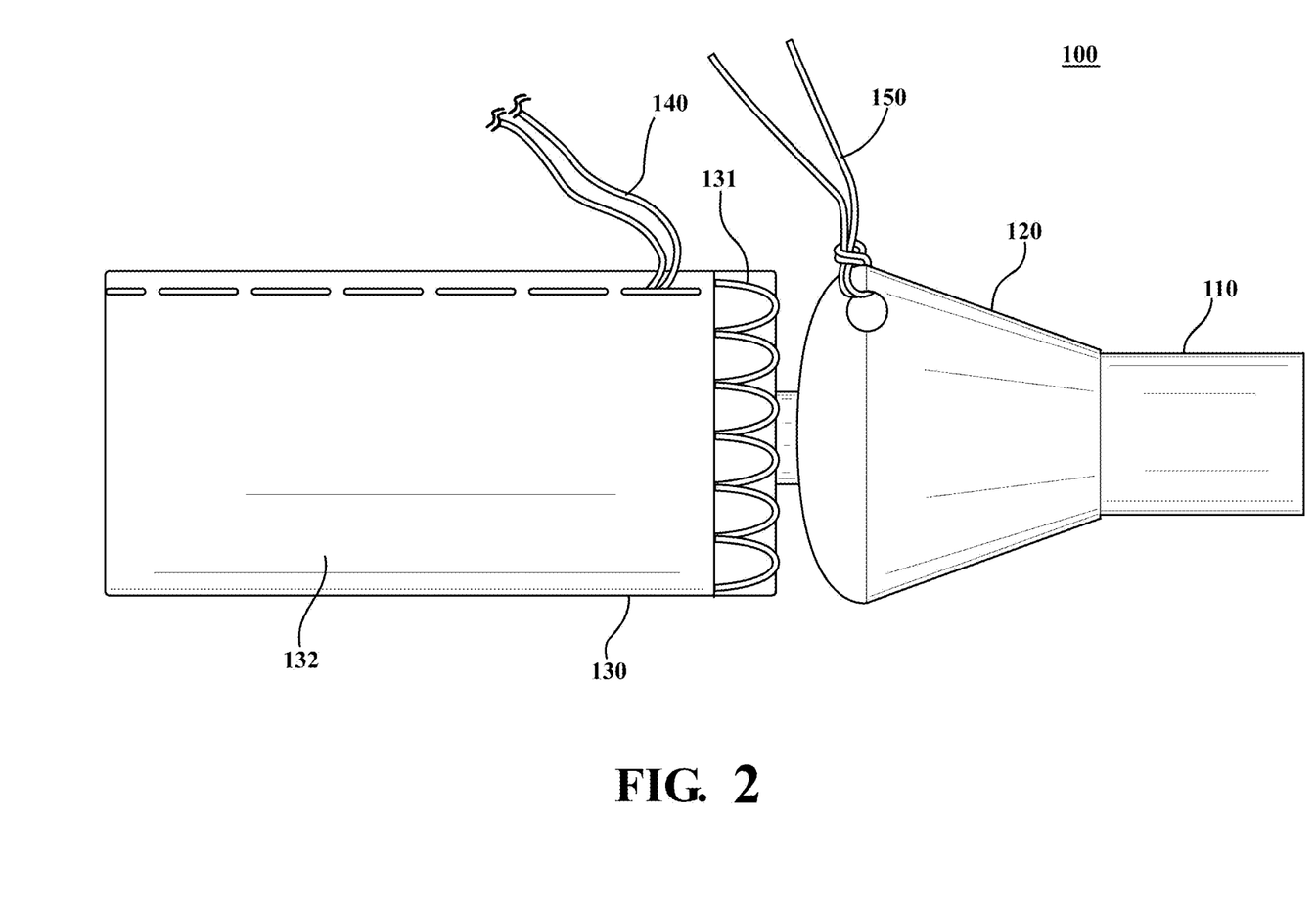
Figure 3:
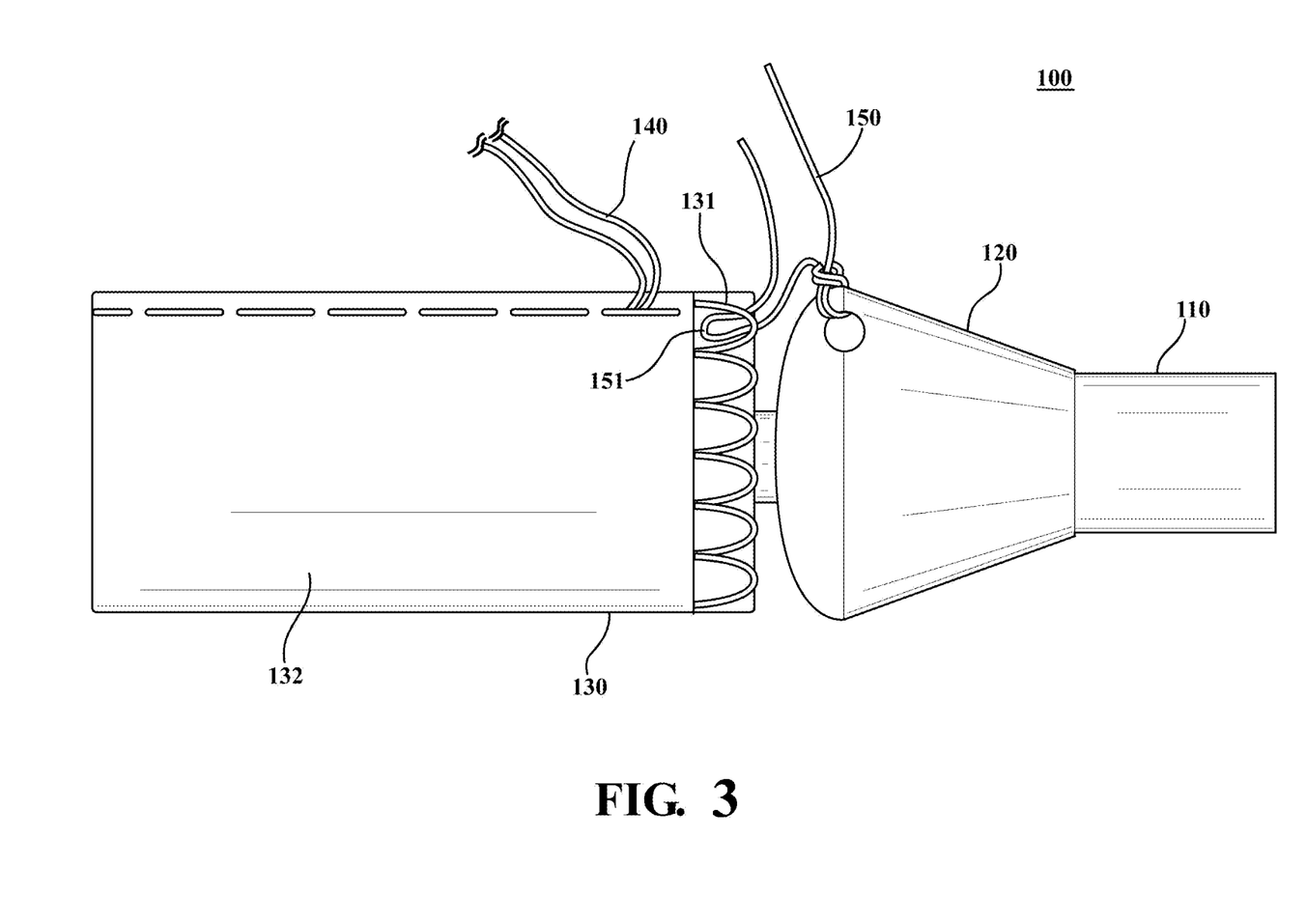
Figure 4:
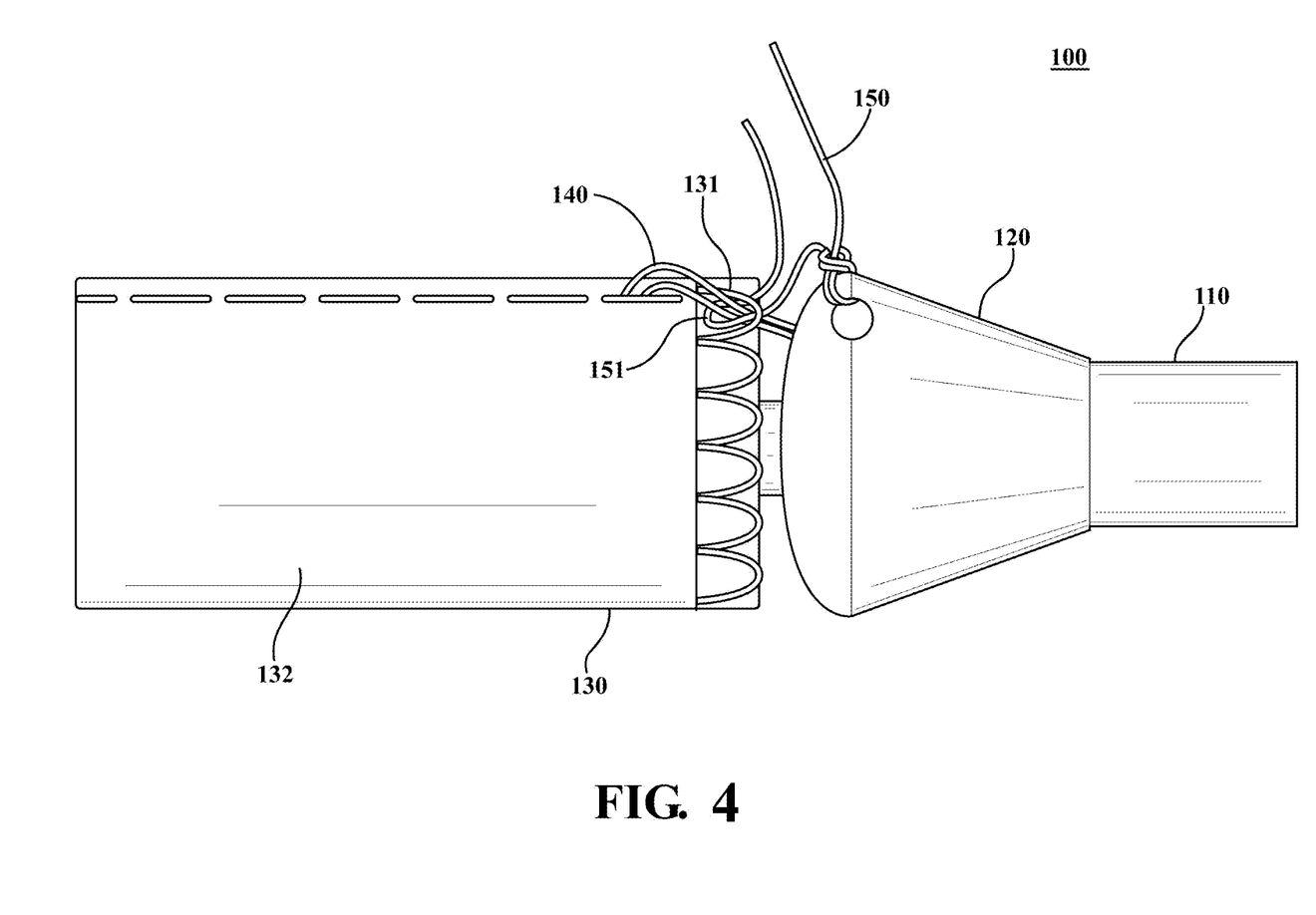
Figure 5:
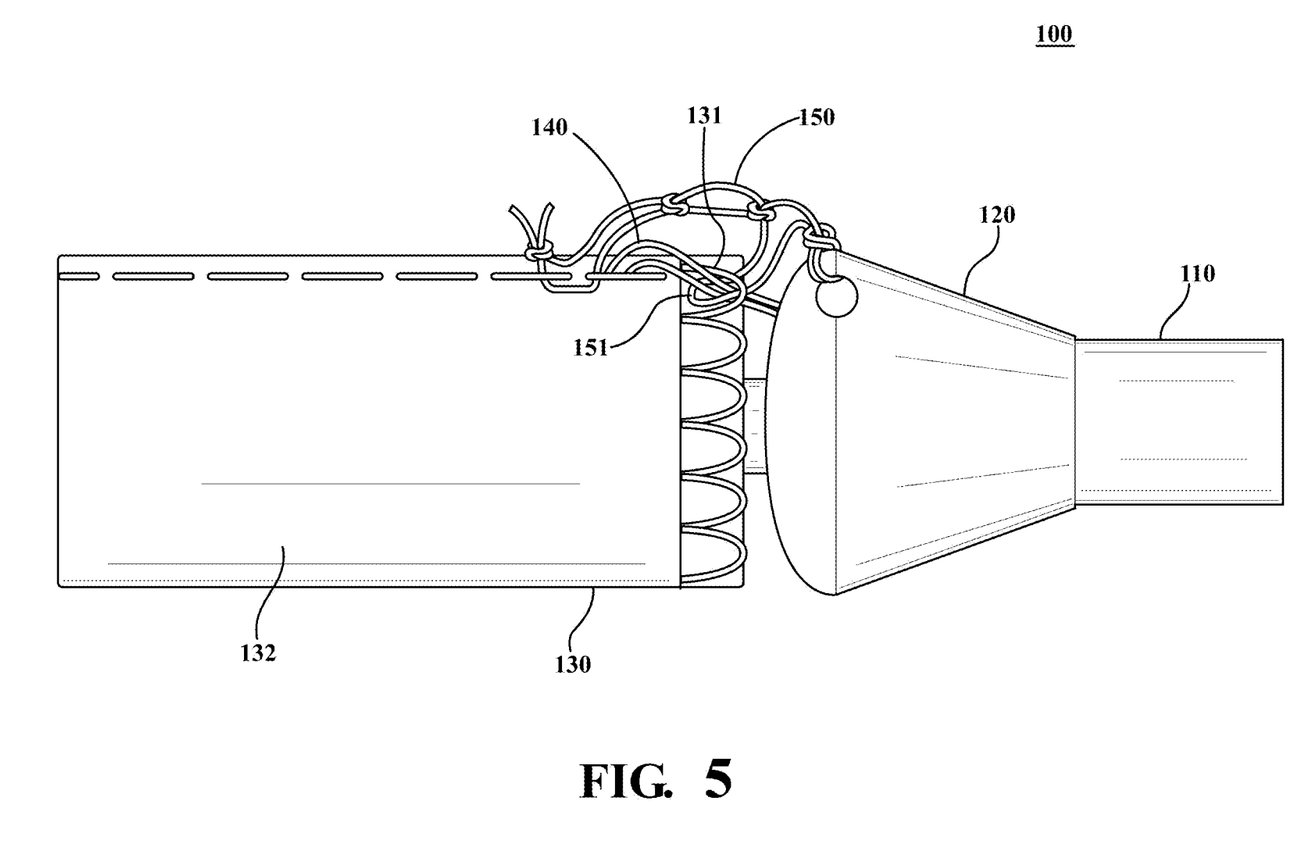

In one embodiment, as illustrated in FIGS. 1-5, the leash line secures both the sheath and the medical device, for example, along the lines set forth above. With reference now to FIGS. 1-5, a medical device delivery system 100 comprises a delivery catheter 110, a deployment sheath 132, a medical device 130 and a leash line 150. Medical device delivery system 100 can further comprise an olive 120 and one or more deployment or release lines 140. For example, in one embodiment, medical device delivery system 100 comprises two (2) release lines 140. In operation, medical device 130 is maintained in a restrained configuration on a delivery catheter 110 and delivered endoluminally through the vasculature toward a treatment site. More specifically, medical device 130 is covered and constrained by deployment sheath 132 during deployment in the restrained configuration. The sheath 132 is held closed by the one or more release lines 140, which further extend through the catheter for access by the clinician. Leash line 150 removably couples the deployment sheath 132 and medical device 130 to delivery catheter 110. More specifically, leash line 150 can couple to delivery catheter 110 at olive 120, which is located at the distal end of delivery catheter 110.

In various embodiments, leash line 150 is releasably coupled to medical device 130 and/or deployment sheath 132 by any suitable method. In one embodiment, leash line 150 comprises a loop 151 for releasably coupling the catheter 110 and the medical device 130. In these embodiments, medical device 130 comprises an apex 131 or other suitable attachment point (e.g., a hole, an eyelet, or other suitable structure). Described in greater detail below, in various embodiments, the loop 151 is releasably coupled to the apex 131 and/or attachment point of medical device 130 to resist unwanted axial displacement of the medical device 130 during deployment or partial deployment of the medical device 130 at or near the treatment site.

In various embodiments, release line 140 couples to and/or threads through deployment sheath 132. After medical device 130 is deployed from delivery catheter 110 in a deployment configuration, release line 140 is retracted through the catheter 110 in the proximal direction to release deployment sheath 132. When deployment sheath 132 is removed, medical device 130 expands to a treatment configuration. When deployed, at least a portion of medical device 130 contacts the wall of a body lumen at the treatment site.

In various embodiments, release line 140 extends through the catheter 110, slidably passes through loop 151, and threads through the deployment sheath 132, as previously described. By this arrangement, the loop 151 is prevented from retracting from the apex 131, thereby maintaining a connection between medical device 130 and leash line 150, until release line 140 is fully retracted through loop 151.

In operation, as release line 140 is removed from deployment sheath 132, deployment sheath 132 begins to release medical device 130. Medical device 130 begins to expand at its distal end as deployment sheath 132 releases, and fully expands as deployment sheath 132 is removed. When deployment sheath 132 releases medical device 130, the expansion of medical device 130 can cause axial or longitudinal movement of medical device 130 in the vasculature. To counteract this longitudinal movement, leash line 150 remains coupled to deployment sheath 132 and medical device 130 while at least a portion of the release line 140 remains extending through the loop 151 in the leash line 150. After full expansion of medical device 130, release line 140 can be retracted into delivery catheter 110 for removal from the vasculature. Retraction of the release line 140 from the loop 151 in the leash line 150 allows retraction of the loop 151 from the apex 131, thereby decoupling or releasing the medical device 130 from the catheter 110. The catheter 110, along with the leash line 150, can then be removed from the treatment site.

Finally, in various embodiments, one or more release lines can be threaded through the deployment sheath at the approximate midway point of the medical device. During deployment, as the release lines are retracted in the proximal direction, the deployment sheath initially releases at the center of the medical device, causing the medical device to initially expand. As the release lines are further retracted, the deployment sheath releases the proximal and distal ends of the medical device, allowing the device to fully deploy and engage the vasculature. The medical device can be retained by the leash line during deployment to facilitate proper positioning of the medical device at the desired treatment site.

It should be appreciated that loop 151 can be releasably coupled to the medical device 130 by other suitable arrangements. In alternative embodiments, for example, the loop 151 can be retained and released in apex 131 or attachment point by the compression of medical device 130 upon crushing of medical device 130 by the deployment sheath and expansion of medical device 130 upon deployment at or partial deployment near the treatment site, respectively. In these embodiments, the loop 151 should have sufficient length to remain engaged with the apex or attachment point so as to resist undesired axial or longitudinal shifting of the device prior to full deployment at the treatment site.

In the various embodiments described herein, each of the delivery catheter, olive, medical device, deployment sheath, release line, leash line and other components of the medical device delivery system (collectively, the "medical device delivery system components"), described above, are highly biocompatible. As used herein, a "biocompatible material" is a material suited for and meeting the purpose and requirements of a medical device, used for either long or short term implants or for non-implantable applications. Long term implants are defined as items implanted for more than 30 days. These support structures, coatings, and secondary structures are preferably formed of a fluoropolymer such as ePTFE. Alternatively, or in combination with a fluoropolymer, the support structures, coatings, and secondary structures can be formed of biocompatible materials, such as polymers, which can include fillers such as metals, carbon fibers, Dacron, glass fibers or ceramics. Such polymers can include olefin polymers, polyethylene, polypropylene, polyvinyl chloride, polytetrafluoroethylene which is not expanded, fluorinated ethylene propylene 45 copolymer, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, such as fully or partially halogenated polyethers, copolymers, and combinations thereof. Also, polyesters, including polyethylene terephthalate (PET) polyesters, polypropylenes, polyethylenes, polyurethanes, polyolefins, polyvinyls, polymethylacetates, polyamides, naphthalane dicarboxylene derivatives, and natural silk can be included in medical device delivery system components.

The medical device delivery system components can be utilized with bio-active agents. Bio-active agents can be coated onto a portion or the entirety of the medical device delivery system components for controlled release of the agents once the medical device delivery system components are implanted. The bio-active agents can include, but are not limited to, vasodilator, anti-coagulants, such as, for example, warfarin and heparin. Other bio-active agents can also include, but are not limited to agents such as, for example, anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); anti-platelet agents such as G(GP) IIb/IIIa inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

As used herein, the term "bio-resorbable" includes a suitable bio-compatible material, mixture of materials or partial components of materials being degraded into other generally non-toxic materials by an agent present in biological tissue (i.e., being bio-degradable via a suitable mechanism, such as, for example, hydrolysis) or being removed by cellular activity (i.e., bioresorption, bioabsorption, or bioresorbable), by bulk or surface degradation (i.e., bioerosion such as, for example, by utilizing a water insoluble polymer that is soluble in water upon contact with biological tissue or fluid), or a combination of one or more of the bio-degradable, bio-erodable, or bio-resorbable material noted above. Potential materials for the stent described herein include, for example, biodegradable polymers such as polylactic acid, i.e., PLA, polyglycolic acid, i.e., PGA, polydioxanone, i.e., PDS, polyhydroxybutyrate, i.e., PHB, polyhydroxyvalerate, i.e., PHV and copolymers or a combination of PHB and PHV (available commercially as Biopol®, polycaprolactone (available as Capronor®), polyanhydrides (aliphatic polyanhydrides in the back bone or side chains or aromatic polyanhydrides with benzene in the side chain), polyorthoesters, polyaminoacids (e.g., poly-L-lysine, polyglutamic acid), pseudo-polyaminoacids (e.g., with back bone of polyaminoacids altered), polycyanocrylates, or polyphosphazenes; as well as bioresorbable metals or metal alloys.

Thus, the medical device delivery system described herein provides a mechanism to place a medical device at a treatment site and limit axial or longitudinal movement during deployment.

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

Likewise, numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. A medical device delivery system comprising:
   a catheter;
   an expandable device disposed on an end of the catheter;
   a sleeve disposed around the expandable device and being configured to cover and releasably constrain the expandable device;
   a release line extending through the sleeve, the release line being configured to hold the sleeve closed and being removable to release the sleeve and allow expansion of the expandable device; and
   a leash line forming a releasable interconnection between the catheter and the expandable device, the leash line having a loop for receiving the release line therethrough and retaining the interconnection between the catheter and the expandable device after removal of the release line from the sleeve.

2. The medical device delivery system of claim 1, wherein the leash line extends through an aperture in the expandable device to form the loop that receives the release line therethrough to retain the expandable device after retraction of the release line.

3. The medical device delivery system of claim 2, wherein the aperture is formed in an end of the expandable device.

4. The medical device delivery system of claim 3, wherein the expandable device comprises a stent, the stent having an apex, the leash line extending through the apex to form the loop.

5. The medical device delivery system of claim 1, wherein the catheter further comprises an olive, and wherein the olive comprises an attachment point configured to receive the leash line.

6. The medical device delivery system of claim 5, wherein the leash line is looped through the attachment point.

7. The medical device delivery system of claim 6, wherein the olive and the leash line are withdrawn after deployment of the expandable device.

8. The medical device delivery system of claim 1, wherein the leash line comprises: a plurality of segments defined by knots; and the loop configured to couple to the expandable device, wherein the loop is provided at a first segment defined between a first knot and a second knot, and wherein the loop passes through an apex of the expandable device.

9. The medical device delivery system of claim 8, wherein the leash line is configured to decouple from an end of the medical device delivery system.

10. The medical device delivery system of claim 9, wherein the leash line is withdrawn with the catheter in response to the expandable device being deployed at a treatment site.

11. The medical device delivery system of claim 8, wherein the leash line is configured to reduce longitudinal movement of the expandable device during deployment at a treatment site.

12. The medical device delivery system of claim 8, wherein the release line is configured to freely slide through the loop.

13. The medical device delivery system of claim 8, wherein the expandable device is deployed to a treatment site in a deployment configuration and expanded at the treatment site in response to removing the release line from the sleeve.

14. The medical device delivery system of claim 13, wherein the loop is decoupled from the expandable device in response to the expandable device being expanded.

15. The medical device delivery system of claim 8, wherein the sleeve is actuated by a release line.

16. A method of deploying a medical device, comprising:
   providing a medical device delivery system, comprising a catheter, a medical device, a deployment sheath surrounding a portion of the medical device and configured to constrain the medical device for delivery to the treatment site, a release line, and a leash line, wherein the medical device is delivered to a treatment site by the catheter, and wherein the leash line couples the medical device to the catheter;
   deploying the medical device from the catheter at the treatment site, wherein the leash line couples to the medical device at two points such that the medical device is stabilized at the treatment site by the leash line;
   retracting the release line through a loop in the leash line and through the catheter, wherein the medical device expands to a treatment configuration in response to retraction of the release line; and
   decoupling the loop of the leash line from the expanded medical device.

17. The method of claim 16, further comprising: releasing the deployment sheath in response to retracting the release line.

18. The method of claim 16, wherein the medical device is at least one of a stent and a stent graft, and wherein the medical device comprises an apex that is capable of receiving the loop.

19. The method of claim 16, wherein the leash line comprises a plurality of knots defining segments, and wherein the loop is defined in a first segment.

20. A medical device delivery system comprising:
   a catheter;
   an expandable device disposed on an end of the catheter;
   a sheath including a plurality of holes and disposed around the expandable device and being configured to cover and releasably constrain the expandable device, the sheath being axially displaceable; and
   a release line arranged through the plurality of holes configured to releasably constrain the sheath; and
   a leash line having a loop for receiving the release line therethrough and forming a releasable connection between the catheter and the device that limits axial displacement of the expandable device relative to the catheter during deployment of the expandable device and that is releasable after deployment of the expandable device.

21. The medical device as set forth in claim 20, wherein the sheath is formed from a flexible fluoropolymer film.

22. The medical device as set forth in claim 21, wherein the sheath is formed from ePTFE.

* * * * *